United States Patent
Manzke et al.

(10) Patent No.: US 9,554,728 B2
(45) Date of Patent: Jan. 31, 2017

(54) VISUALIZATION FOR NAVIGATION GUIDANCE

(75) Inventors: Robert Manzke, Bonebuttel (NL); Patrick Etyngier, Plaisir (FR); Pascal Yves Francois Cathier, Asnieres-sur-Seine (FR); Nicolas Francois Villain, Rueil-Malmaison (FR); Volker Rasche, Erbach (DE); Kawaldeep Singh Rhode, Croydon (GB)

(73) Assignees: KONINKLIJKE PHILIPS N.V., Eindhoven (NL); KING'S COLLEGE LONDON, London (GB)

( * ) Notice: Subject to any disclaimer, the term of this patent is extended or adjusted under 35 U.S.C. 154(b) by 8 days.

(21) Appl. No.: 14/002,368

(22) PCT Filed: Mar. 1, 2012

(86) PCT No.: PCT/IB2012/050966
§ 371 (c)(1),
(2), (4) Date: Aug. 30, 2013

(87) PCT Pub. No.: WO2012/117366
PCT Pub. Date: Sep. 7, 2012

(65) Prior Publication Data
US 2013/0336558 A1 Dec. 19, 2013

(30) Foreign Application Priority Data
Mar. 2, 2011 (EP) .................................. 11305225

(51) Int. Cl.
*G06K 9/00* (2006.01)
*A61B 5/06* (2006.01)
(Continued)

(52) U.S. Cl.
CPC ................. *A61B 5/066* (2013.01); *A61B 6/12* (2013.01); *A61B 6/503* (2013.01); *A61B 6/5235* (2013.01);
(Continued)

(58) Field of Classification Search
None
See application file for complete search history.

(56) References Cited

U.S. PATENT DOCUMENTS 6,248,070 B1   6/2001   Kanda
6,650,927 B1 * 11/2003   Keidar .......................... 600/424
(Continued)

FOREIGN PATENT DOCUMENTS

EP   1182619 A2   2/2002
EP   1720039 A2   11/2006
(Continued)

OTHER PUBLICATIONS

Termeer Maurice et al., "Patient-Specific Coronary Artery Supply Territory AHA Diagrams", Journal of Cardiovascular Magnetic Resonance 2009, 11(Suppl 1), Abstracts of the 12th Annual SCMR Scientific Sessions, Jan. 2009, pp. 164-165 http://jcmr-online.com/supplements/11/S1.

*Primary Examiner* — Feng Niu (57) ABSTRACT

The present invention relates to visualizing information of an object. In order to provide spatial information and in addition situation specific data to the user while ensuring an effective perceptibility, a method (110) is provided comprising the steps of: a) providing (112) pre-navigation data (114) of a region of interest of an object (22); wherein the pre-navigation data comprises spatial geometrical data (116) and a functional parameter surface (118) in correspondence to the spatial geometrical data; b) acquiring (120) live image data (122) of the region of interest; c) detecting (124) an element (126) in the live image data; d) determining (128)
(Continued)

spatial relation (130) of the pre-navigation data and the live image data; e) determining (132) the position (134) of the detected element in the spatial geometrical data, which determining is based on the spatial relation, and computing (136) a predetermined related point of location (138) on the functional parameter surface; f) generating (140) a combination (142) of a simplified surface representation (144) of the region of interest, which simplified surface representation is based on a visualization of the functional parameter surface, and a marker (146) indicating the computed predetermined related point of location; and g) displaying (148) the combination as navigation guidance (150).

19 Claims, 9 Drawing Sheets

(51) Int. Cl.
 *A61B 6/12* (2006.01)
 *A61B 6/03* (2006.01)
 *A61B 6/00* (2006.01)
(52) U.S. Cl.
 CPC ........... *A61B 90/37* (2016.02); *A61B 6/032* (2013.01); *A61B 6/488* (2013.01); *A61B 2034/2065* (2016.02); *A61B 2090/364* (2016.02); *A61B 2090/376* (2016.02)

(56) References Cited

U.S. PATENT DOCUMENTS

| | | |
|---|---|---|
| 2004/0171922 A1 | 9/2004 | Rouet |
| 2005/0058328 A1 | 3/2005 | Moreau-Gobard |
| 2005/0197568 A1 | 9/2005 | Vass |
| 2006/0045328 A1 | 3/2006 | Jacob |
| 2006/0182341 A1 | 8/2006 | Rinck |
| 2006/0235294 A1 | 10/2006 | Florin |
| 2006/0253029 A1* | 11/2006 | Altmann et al. ............ 600/466 |
| 2006/0262970 A1 | 11/2006 | Boese |
| 2007/0167706 A1 | 7/2007 | Boese |
| 2008/0118121 A1 | 5/2008 | Skinner |
| 2008/0281195 A1 | 11/2008 | Heimdal |
| 2009/0208079 A1 | 8/2009 | Vaillant |
| 2010/0217116 A1 | 8/2010 | Eck |
| 2014/0023250 A1* | 1/2014 | Cathier et al. ............ 382/128 |

FOREIGN PATENT DOCUMENTS

| | | |
|---|---|---|
| EP | 1837828 A2 | 9/2007 |
| JP | 3332191 A | 12/1996 |
| JP | 2002119507 A | 4/2002 |
| JP | 2010075554 A | 4/2010 |
| WO | WO2006103644 A1 | 10/2006 |
| WO | WO2008065581 A2 | 6/2008 |
| WO | WO2008107814 A1 | 9/2008 |

* cited by examiner

VISUALIZATION FOR NAVIGATION GUIDANCE

CROSS-REFERENCE TO PRIOR APPLICATIONS

This application is the U.S. National Phase application under 35 U.S.C. §371 of International Application Ser. No. PCT/IB2012/050966, filed on Mar. 1, 2012, which claims the benefit of European Application Serial No. 11305225.2, filed on Mar. 2, 2011. These applications are hereby incorporated by reference herein.

FIELD OF THE INVENTION

The present invention relates to visualizing information of an object, in particular to a method for visualizing information of an object of interest, a device for visualizing, a medical imaging system for visualizing as well as to a computer program element and a computer readable medium.

BACKGROUND OF THE INVENTION

To visualize information about a situation of an object, for example a patient, it is known to overlay two-dimensional live images to preoperative images. The preoperative image data contains information, for example, about the vascular structure, whereas the 2D live image provides information about the current situation. For example, in document WO 2008/107814 A1, a method is described to provide a user with such information. However, the information thus presented only provides limited information, for example for cardiovascular interventional guidance. However, with the development of new examination and treatment procedures, for example for interventional cardiovascular procedures, specifically, for complex procedures such as ablations and device implantations in cardiac electrophysiology, the demand for provided information increases constantly.

SUMMARY OF THE INVENTION

Thus, there may be a need to provide spatial information and in addition situation specific data to the user while ensuring an increased perceptibility.

In the present invention, this is solved by the subject-matter of the independent claims, wherein further embodiments are incorporated in the dependent claims.

It should be noted that the following described aspects of the invention apply also for the device for visualizing information of an object of interest, the medical imaging system for visualizing information of an object of interest, the computer program element, and the computer readable medium.

According to an exemplary embodiment of the invention, a method for visualizing information of an object of interest is provided that comprises the following steps:

a) providing pre-navigation data of a region of interest of an object, wherein the pre-navigation data comprises spatial geometrical data and a functional parameter surface in correspondence to the spatial geometrical data;

b) acquiring live image data of the region of interest;

c) detecting an element in the live image data;

d) determining spatial relation of the pre-navigation data and the live image data;

e) determining the position of the detected element in the spatial geometrical data, which determining is based on the spatial relation, and computing a predetermined related point of location on the functional parameter surface;

f) generating a combination of a simplified surface representation of the region of interest, which simplified surface representation is based on a visualization of the functional parameter surface, and a marker indicating the computed predetermined related point of location; and g) displaying the combination as navigation guidance.

According to a further exemplary embodiment of the invention, a device is provided, comprising a processing unit, an interface unit, and a display.

The interface unit is adapted to provide pre-navigation data of a region of interest of an object, wherein the pre-navigation data comprises spatial geometrical data and a functional parameter surface in correspondence to the spatial geometrical data. The interface unit is further adapted to provide live image data of the region of interest.

The processing unit is adapted to detect an element in the live image data. The processing unit is further adapted to determine spatial relation of the pre-navigation data and the live image data. The processing unit is also adapted to determine the position of the detected element in the spatial geometrical data, which determining is based on the spatial relation, and to compute a predetermined related point of location on the functional parameter surface. The processing unit is still further adapted to generate a combination of a simplified surface representation of the region of interest, which simplified surface representation is based on a visualization of the functional parameter surface, and a marker indicating the computed predetermined related point of location.

The display is adapted to display the combination as navigation guidance.

According to a further exemplary embodiment of the invention, a medical imaging system for visualizing information of an object of interest is provided, comprising a device according to the above mentioned exemplary embodiment, and image acquisition means. The image acquisition means are adapted to acquire the live image data.

It can be seen as a gist of the invention to provide both spatial information and functional information. Both types of information are provided in one image in form of the navigation guidance. To allow for a quick understanding that does not require complex imagination on the side of the user, a simplified surface representation is chosen wherein the functional parameter surface is visualized, and the marker provides the spatial information about the current situation.

These and other aspects of the present invention will become apparent from and elucidated with reference to exemplary embodiments described hereinafter.

BRIEF DESCRIPTION OF THE DRAWINGS

Exemplary embodiments of the invention will be described in the following with reference to the following drawings.

DETAILED DESCRIPTION OF EXEMPLARY EMBODIMENTS

Figure 1:
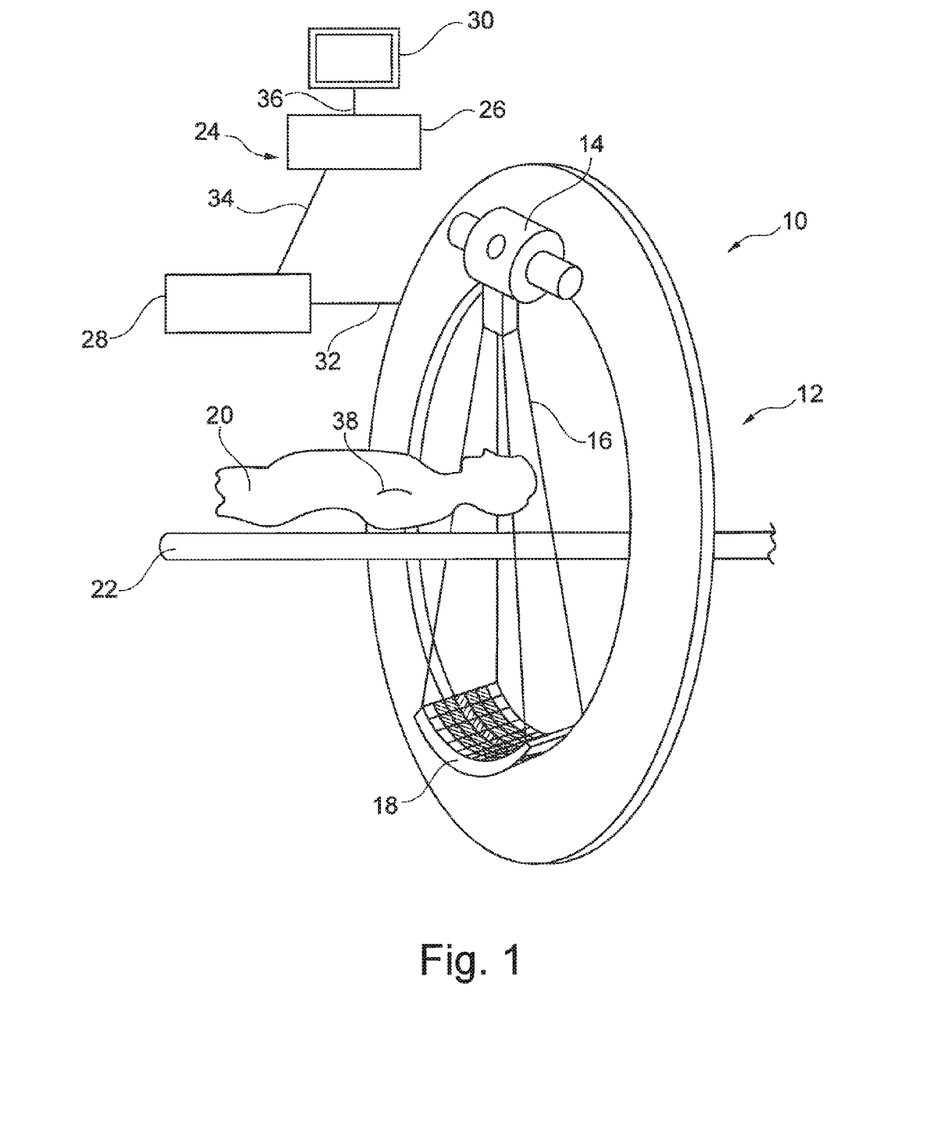
FIG. 1 illustrates a medical imaging system with a device according to an exemplary embodiment of the invention.

FIG. 1 schematically shows a medical image system 10, for the use in cardiovascular laboratory, for example. The medical image system 10 for visualizing information of an object of interest comprises image acquisition means 12. For example, the image acquisition means 12 are X-ray image acquisition means provided with a source of X-ray radiation 14 to generate X-ray radiation, indicated by an X-ray beam 16. Further an X-ray image detection module 18 is located opposite the source of X-ray radiation 14 such that, for example, during a radiation procedure, an object, for example a patient 20, can be located between the source of X-ray radiation 14 and the detection module 18. Further a table 22 is provided to receive the object to be examined, i.e. a patient 20.

According to another exemplary embodiment, although not shown, the medical image system 10 comprises image acquisition means 12 in form of ultrasound image acquisition means. Of course, in case of ultrasound image acquisition means, the source of X-ray radiation, the X-ray beam 16, as well as the image detection module 18 are replaced by an ultrasound transducer emitting ultrasound waves into the object, for example the patient, and receiving reflected ultrasound waves.

According to a further exemplary embodiment, the image acquisition means 12 acquire spatial geometrical data by MR (Magnetic Resonance Imaging MRI) or NMRI (Nuclear Magnetic Resonance Imaging). Of course, other nuclear imaging such as SPECT (Single Photon Emission Computed Tomography) or PET (Positron Emission Tomography) is also provided in exemplary embodiments (not shown).

Further, the medical image system 10 of FIG. 1 comprises a device 24 for visualizing information of an object. The device 24 comprises a processing unit 26, an interface unit 28, and a display 30.

The interface unit 28 is adapted to provide pre-navigation data of a region of interest of an object, wherein the pre-navigation data comprises spatial geometrical data and a functional parameter surface in correspondence to the spatial geometrical data. The interface unit 28 is further adapted to provide live image data of the region of interest.

The processing unit 26 is adapted to detect an element in the live image data. The processing unit 26 is also adapted to determine spatial relation of the pre-navigation data and the live image data. The processing unit 26 is also adapted to determine the position of the detected element in the spatial geometrical data, which determining is based on the spatial relation, and to compute a predetermined related point of location on the functional parameter surface. The processing unit 26 is still further adapted to generate a combination of a simplified surface representation of the region of interest, which simplified surface representation is based on a visualization of the functional parameter surface, and a marker indicating the computed predetermined related point of location.

The display 30 is adapted to display the combination as navigation guidance.

Further, the acquisition means 12 are adapted to acquire the live image data.

The acquired live image data is then provided to the interface unit 28 which is indicated by the first connecting line 32. The interface unit 28 then provides the live image data to the processing unit which is indicated by a second connecting line 34. The generated combination is provided by the processing unit 26 to a display 30 which is indicated by a third connecting line 36. Of course, the data connections of the above mentioned units and means can also be realized with a wireless connection.

It is noted that the example shown is a so-called CT-image acquisition device. Of course, the invention also relates to other types of X-ray image acquisition means, such as a C-arm X-ray image acquisition device with a C-arm instead of a circular gentry, as shown in FIG. 1.

Figure 2:
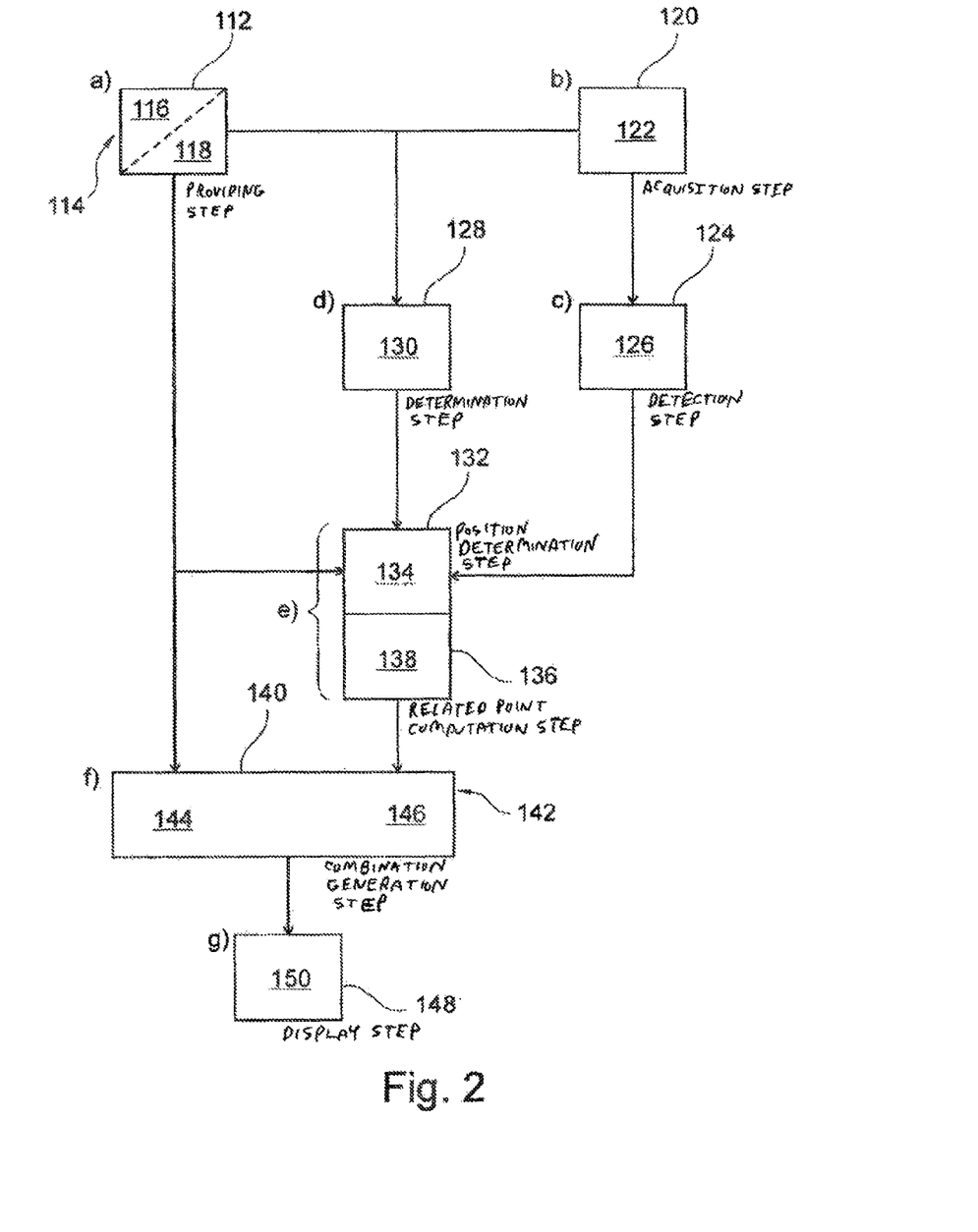
FIG. 2 schematically illustrates the basic steps of an exemplary embodiment of the invention.

The procedure according to the invention is described in more detail below with reference to FIG. 2.

First, in a providing step 112, pre-navigation providing data 114 of a region of interest of an object 22 is provided. The pre-navigation data 114 comprises spatial geometrical data 116 and a functional parameter surface 118 in correspondence to the spatial geometrical data 116, wherein the term "correspondence" relates to spatial correspondence.

Further, in an acquisition step 120, live image data 122 of the region of interest is acquired.

In a detection step 124, an element 126 in the live image is detected.

Further, in a determination step 128, spatial relation 130 of the pre-navigation data 114 and the live image data 122 is determined.

In another step, a sub-step determination step 132 is provided in which the position 134 of the detected element in the spatial geometrical data is determined, which determination is based on the spatial relation 130. Further, in a computational sub-step 136, a predetermined related point of location 138 on the functional parameter surface 118 is computed.

Then, in a generating step 140, a combination 142 of a simplified surface representation 144 of the region of interest is generated, wherein the simplified surface representation 144 is based on a visualization of the functional parameter surface 118. Further, in the generating step 140, a marker 146 is generated indicating the computed predetermined related point of location 138.

In a display step 148, the combination is displayed as navigation guidance 150.

It is noted that the steps described above in FIG. 2 are only shown in an exemplary order of the steps. Of course, other orders of the steps are also possible. For example, step d) is performed before step c). Still further, the acquisition steps a) and b) provide image data that are already registered to one another. In such case, further determination of the spatial relation as in step d) is not necessary anymore.

According to a further aspect, the steps can be repeated continuously with a predetermined time rate.

As mentioned above, the spatial geometrical data can be acquired by Computed Tomography.

According to another aspect, the spatial geometrical data is acquired by Ultrasound.

According to a further aspect, the spatial geometrical data 116 is acquired by Magnetic Resonance Imaging or Nuclear Magnetic Resonance Imaging. The spatial geometrical data can also be acquired by Nuclear Imaging such as Single Photon Emission Computed Tomography or Positron Emission Tomography.

According to a further aspect, the spatial geometrical data 116 comprises three-dimensional, i.e. volume information about the region of interest.

According to a further aspect, the spatial geometrical data also comprises temporal information. In other words, as the spatial geometrical data, 3D+t image data or 4D image data is provided.

According to an aspect of the invention, the functional parameter surface comprises a bull's-eye view which is illustrated and described below.

According to a further aspect, the functional parameter surface comprises a three-dimensional mesh view.

According to a further aspect, the functional parameters refer to anatomy locations of the object, i.e. the patient.

According to a further aspect, the functional parameter surface is in a known spatial relation to the spatial geometrical data.

For example, for registering the spatial geometrical data and the functional parameter surface, the same imaging modality is used for acquiring the spatial geometrical data and the functional parameter surface.

According to another aspect of the invention, different imaging modalities are used for acquiring the spatial geometrical data and the functional parameter surface.

It is noted that in the context of describing the present invention, the providing step 112 is also referred to as step a), the acquisition step 120 as step b), the detection step 124 as step c), the determination step 128 as step d), the determination step 132 as step e), the generating step 140 as step f), and the displaying step 148 as step g).

According to a further aspect of the invention, the object of interest comprises a tubular structure, for example a vascular structure. For example, an active area of research is advanced guidance methods or interventional cardiovascular procedures. Specifically, for complex procedures such as ablations and device implantations in cardiac electrophysiology (EP), according to the invention, the pre-procedural imaging information can be registered and overlaid to the interventional X-ray images.

According to an aspect of the invention, the location of an element, for example a catheter, guide wire or lead is visualized in relation to the target zones for ablation or pacer lead deployment.

Figure 3:
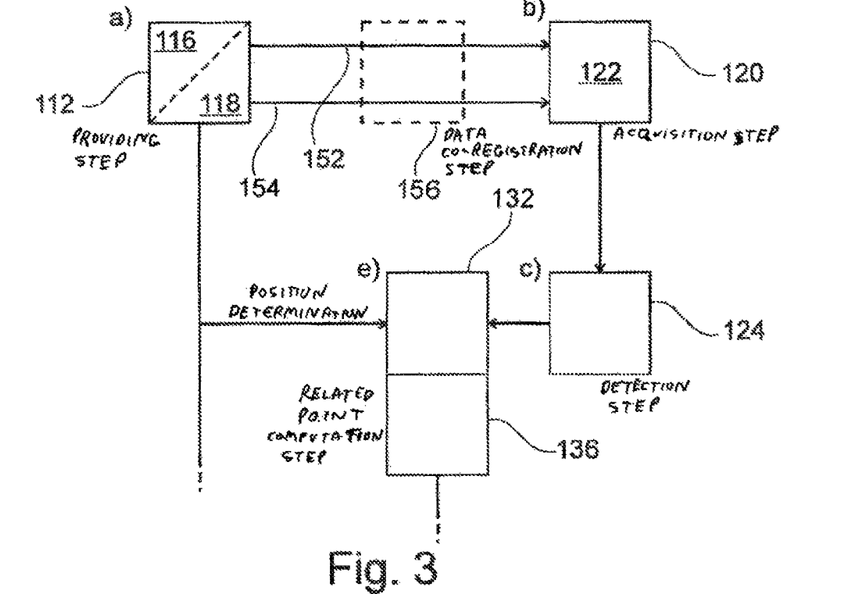
FIGS. 3 to 8 show method steps of further exemplary embodiments.

According to a further aspect, the functional parameter surface 118 and the spatial geometrical data 116 of the providing step 112 are each registered to the live image data 122 of the acquisition step 120, which is indicated by a first arrow 152 and a second arrow 154. The step of registering the two types of data is further indicated by a box overlaid to the first and second arrow 152, 154, which box is illustrated with a dashed line, indicated with reference numeral 156.

According to an aspect of the invention, for cardiac examination, the functional parameters of the functional parameter surface 118 comprise, for example, at least one of the groups or a combination thereof, comprising scar location and burden, mechanical function, electrical activation, perfusion/viability or others. The functional parameters can also comprise any combination of parameters calculated there from.

Whereas the element 126 is detected in the live image data 122, according to a further aspect, the element can also be visible in the spatial geometrical data 116.

With respect to step b), according to an aspect of the invention, the live image data 122 comprises 2D image data, for example 2D fluoroscopy images.

According to a further aspect, the live image data 122 also comprises spatial geometrical data.

With respect to step c), the detection 124 comprises tracking the element in a sequence of live images acquired in step b).

According to an aspect of the invention, the element is constrained to move inside a sub-volume of the region of interest, for example inside a tubular structure, such as a vessel tree. This provides the advantage, that in case such a sub-volume is provided in the acquired live image data, for example by image analysis, the element can be located only inside such a volume as a vessel tree, for example, which leads to an improvement of the detection of the element.

Figure 4:
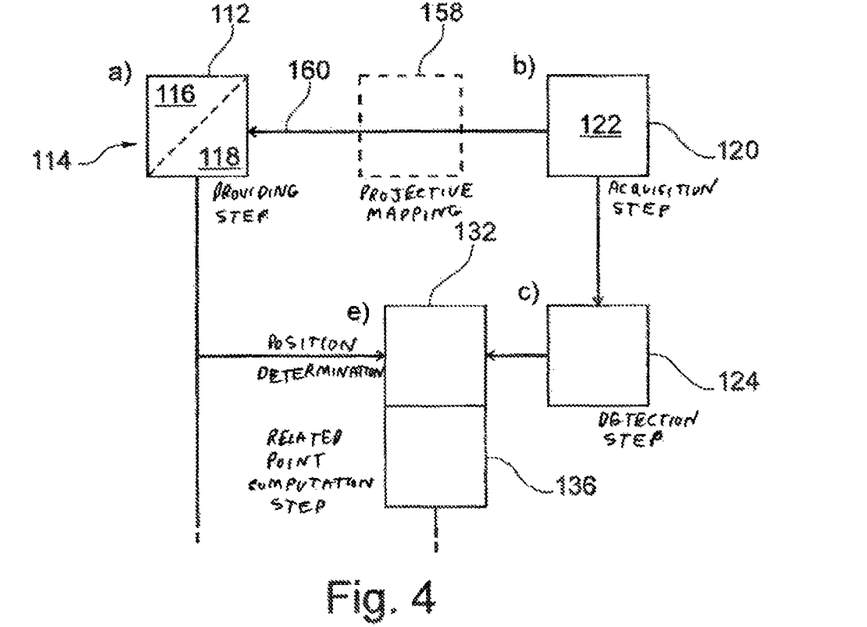

With respect to step d), the determination 128 may comprise projective mapping 158 of the element in the live image data into the spatial geometrical data, which is indicated by a mapping box shown in a dotted line and an arrow 160 from step b) to step a), i.e. from the acquisition box 120 to the providing box 112.

According to a further aspect, step d) comprises registering the spatial geometrical data 116 and the live image data 122.

According to a further aspect, step d) comprises a 2D-3D registration based on at least three marker points that are determined in the live image data and that are determined in the spatial geometrical data (not shown).

According to a further aspect, step d) comprises a registration based on image intensity.

According to a further aspect, step d) of determining the spatial relation 130 comprises localizing the element.

For example, the spatial relation 130 is based on registering the element.

According to a further aspect, the spatial relation 130 is based upon registering landmarks.

For example, the spatial relation can also be achieved by using the same imaging modality for acquiring the spatial geometrical data 116 and the live image data 122.

According to a further aspect, step d) comprises correcting for misalignment, for example breathing or cardiac motion compensation.

According to a further aspect, in case that the spatial geometrical data 116 also comprises temporal information, for the determination of the spatial relation, a temporal spatial relation is determined, although not further shown.

With respect to step e), according to a further aspect, the predetermined relation can be preset by the user.

According to a further aspect, the predetermined relation comprises at least one parameter.

According to an exemplary embodiment of the invention, the predetermined related point of location is the closest point.

Figure 5:
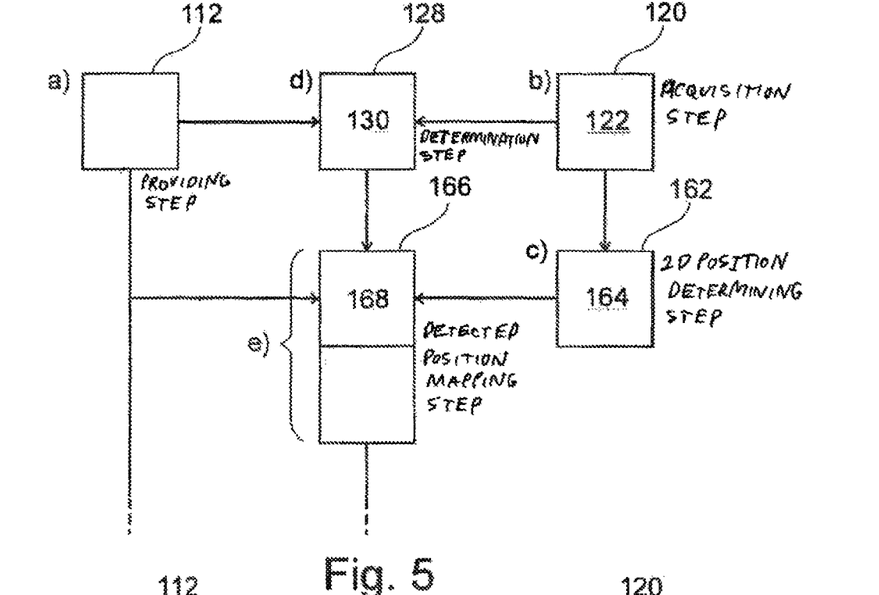

According to a further exemplary embodiment, shown in FIG. 5, the detection of the element in step c) comprises determining 162 the 2D position 164 of the element in the live image data and for determining the position in step e), the detected 2D position is mapped 166 to the spatial geometrical data 116 by a direct projection line 168.

According to a further aspect, for determining the position, spatial parameters are provided by acquisition means. For example, the spatial parameters are provided by electromagnetic localization or with one or two 2D images with different viewing planes.

According to a further aspect, step e) comprises correcting for misalignment, for example breathing or cardiac motion compensation.

Figure 6:
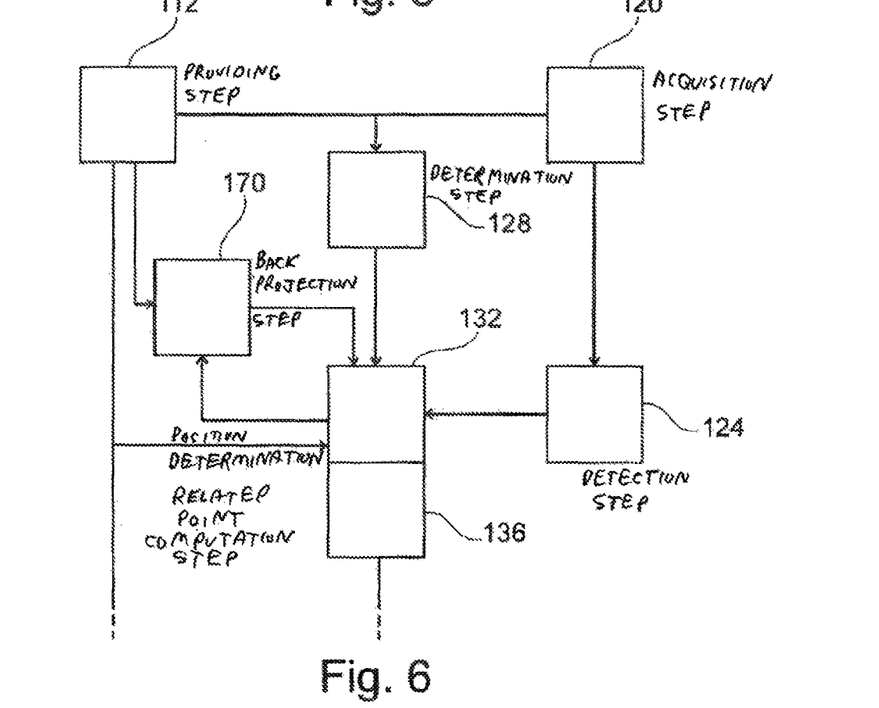

According to a further exemplary embodiment, shown in FIG. 6, step e) comprises a back projection 170 of the tracked location through the spatial geometrical data, to estimate spatial position 172 of the element.

According to an exemplary aspect, this can be performed in a loop-like manner, indicated by two arrows 174a and 174b entering and leaving the back projection box 170.

According to an exemplary embodiment of the invention, in case that the back projection does not intersect with the anatomy according to the spatial geometrical data 116, the closest or statistically most likely point in the anatomy is used (not shown).

According to a further exemplary embodiment, the simplified surface representation is an unfolded map image (examples for an unfolded map image are described further below).

According to a further aspect, the visualizing of functional parameters is also referred to as functional image data.

According to a further aspect, for generating the combination, a 3D image representation of the spatial geometrical data 116 and the determined 3D position are mapped forward into a flat representation (see below).

According to a further aspect, the representation comprises a 2D map with colour coded information as further dimension besides the two geometrical dimensions.

According to a further exemplary embodiment of the invention, a projection axis from the detected element in the spatial geometrical data to the computed related point of location on the functional parameter surface is provided. Further, the simplified surface representation is a 3D image and the 3D image is aligned with the projection axis.

According to a further aspect, step f) comprises computing a marker position in the unfolded representation based on the determined position of step e).

According to a further aspect, the surface representation is also referred to as parametric surface.

According to a further aspect, the unfolded 2D map encodes the information of the functional parameter surface 118, for example a functional mesh.

According to a further aspect, step f) comprises generating a segmented mesh.

According to a further exemplary embodiment of the invention, the unfolded map, as indicated above, is a bull's eye view (see further below for an example of such a bull's eye view).

According to a further aspect, the simplified surface representation comprises a 2D surface map, for example of the left atrium in case of cardiovascular interventions.

Figure 7:
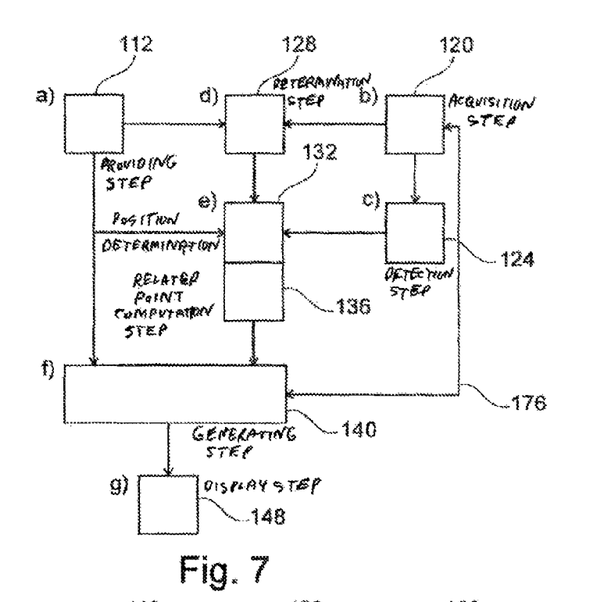

According to a further exemplary embodiment of the invention, step f) comprises combining navigation anatomy with the simplified surface representation 144. For example, as shown in FIG. 7, step f) comprises combining live image data 122 provided in step b) as the navigation anatomy. In FIG. 7, this is indicated by an arrow 176 from the acquisition box 120 to the generating box 140. For example, the navigation anatomy comprises the live image data in form of a fluoroscopic 2D image.

According to a further exemplary embodiment, the navigation anatomy comprises a projection 178 of the vascular structure.

Figure 8:
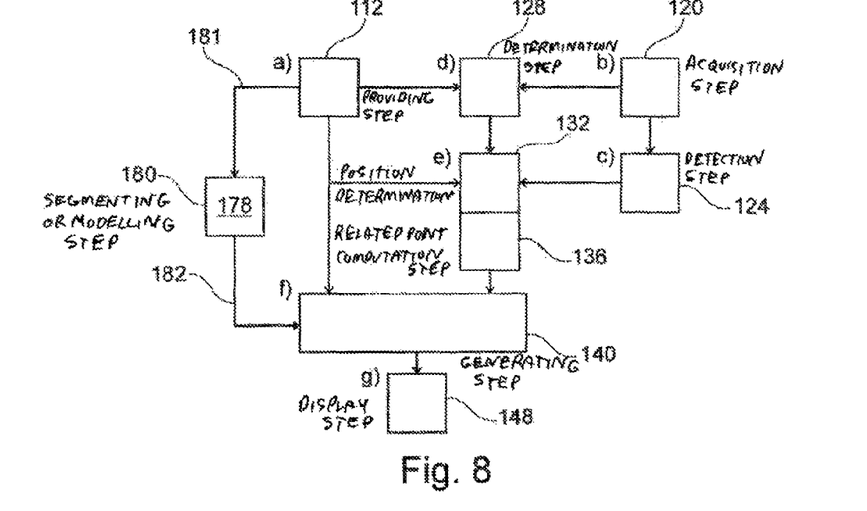

According to an aspect, shown in FIG. 8, the projection 178 is derived by segmenting or modelling 180 the spatial geometrical data 116 provided in step e) which is indicated by an arrow 181 from the box of the providing step 112 to the segmenting or modelling step 180. The projection 178 thus created, or computed respectively, is then entered to the generating box 140 which is indicated by an arrow 182 entering the box of step f).

According to an exemplary embodiment of the invention, the navigation guidance 150 is a 2D representation comprising functional parameter surface information and 3D positioning information of the element in relation to the region of interest. For an example of the 2D representation, see below.

According to an aspect of the invention, the navigation guidance also provides temporal information in case the pre-navigation data comprises 3D+t image data.

Figure 9:
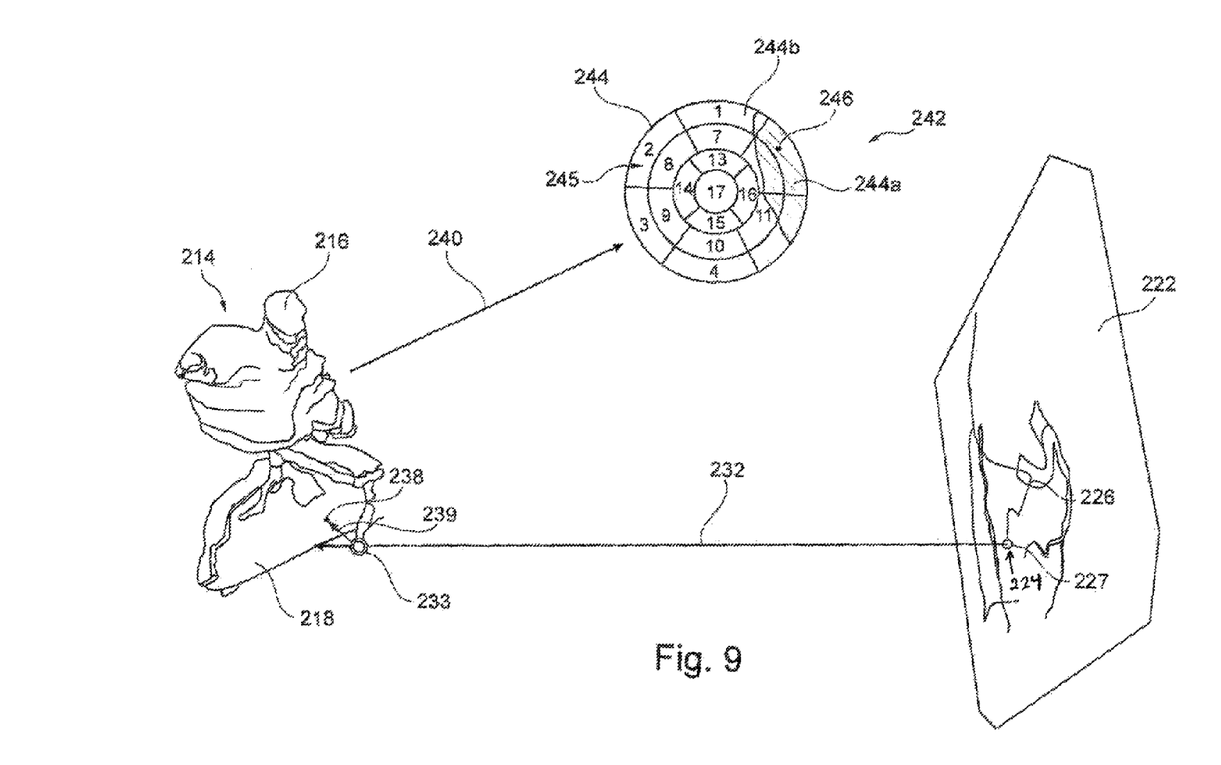
FIG. 9 schematically describes a further exemplary embodiment of the invention.

In the following, an exemplary embodiment of the invention is described with reference to FIG. 9. In the left part of the image, pre-navigation data 214 of a region of interest of an object is provided. The pre-navigation data comprises spatial geometrical data 216, or in other words, the pre-navigation data 214 comprises three-dimensional image data of the region of interest. For example, geometrical data 216 shown in FIG. 9 provides three-dimensional anatomic information, for example in a cardiovascular intervention. The pre-navigation data 214 also comprises a functional parameter surface 218 in correspondence to the spatial geometrical data 216. As an exemplary embodiment, shown in FIG. 9, the functional parameter surface 218 comprises a functional mesh. As can be seen, the functional mesh follows the contour, i.e. the three-dimensional form of the anatomy, and provides additional information about functional parameters, as mentioned above. These functional parameters are provided, for example, by a colour coding. For example, the target area is shown in green, whereas the other surfaces are shown in a red colour. Of course, this can also be achieved by different patterns.

In the right part of FIG. 9, a perspective or slightly distorted live image data 222 of the region of interest is provided, for example in form of a 2D fluoroscopy X-ray image. In the fluoroscopy image 222, an element 226 is visible and can thus be detected. For example, the element 226 is a guide wire with a guide wire or lead tip 227, indicated by a red point, for example. As indicated by a coded line 225, the element 226 has already been detected in FIG. 9.

Further, the spatial relation of the pre-navigation data 214 and the live image data 222 is also already determined. The tip 227 is then taken as a position 224 of the element 226 such that the position 224 of the detected element can be determined in the spatial geometrical data 216. Since the spatial relation of the two types of data is known, the determination is achieved by a line projection in X-ray geometry, which is indicated by a direct arrow 232 from the tip position 224 in direction of the spatial geometrical data 216. As indicated by a point 233, the position of the guide wire in 3D is achieved by projective mapping into the mesh of the constraining anatomy which is representing the spatial geometrical data 216. Thus, the position of the detected element is determined in the spatial geometrical data.

Further, in a computing step, a predetermined related point of location on the functional parameter surface is computed. According to the example shown, the predetermined related point of location can be a closest point 238 on the functional mesh with respect to the detected lead position indicated by point 233. The computing is indicated by an arrow 239.

In order to be able to provide the user with an easily perceptive information, a simplified surface representation 244 of the region of interest is generated. According to the example shown, the simplified surface representation is a so-called bull's-eye representation which is also referred to as a bull's-eye plot. Such a bull's-eye representation shows the volumetric information of the region of interest in a two-dimensional, i.e. flat unfolded map. The individual volumetric parts enclosing the volume in the spatial geometrical data 216 are divided into a number of segments 245, as indicated in the bull's-eye plot in the middle of FIG. 9. The surface parts from the spatial geometrical data 216 are number coded. It is further possible to transfer the computed position into the unfolded map projection by a forward mapping. As can be seen in the simplified surface representation 244, the segments indicated by numbers are also overlaid by coded patterns or colours. For example, the target area is indicated by a certain predetermined pattern 244a whereas the rest is coded with another predetermined coded pattern 244b. The closest point computed in the determination step before is indicated with a marker 246. The forward mapping is indicated by an arrow 240. Thus, a combination 242 is generated which can then be displayed as navigation guidance.

Figure 10:
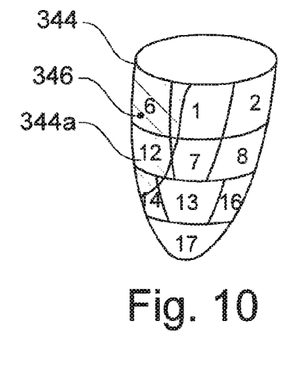
FIGS. 10 to 20 show exemplary embodiments of navigation guidance provided to the user according to the invention.

According to a further aspect of the invention, instead of an unfolded map, for example a bull's-eye view, it is also possible to generate a three-dimensional left ventricle figure as shown in FIG. 10 for the simplified surface representation. According to the reference 15 numbers used with respect to the bull's-eye view, FIG. 10 shows a combination 342 of a simplified surface representation 344 with a marker 346 indicating the computed predetermined related point of location. Further, it is also possible to indicate the target area with a coded pattern 344a.

Figure 11:
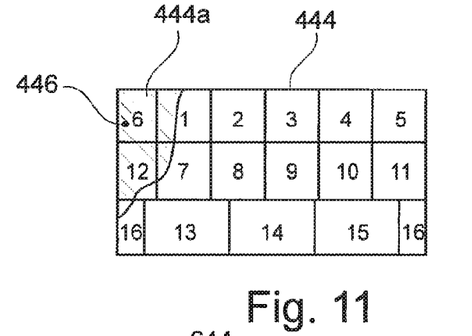

In another example, shown in FIG. 11, the left atrium is shown in an unrolled manner as a simplified surface representation 444 with a marker 446 indicated the computed predetermined related point of location, and also a target area indicated with a coded pattern 444a.

Figure 12:
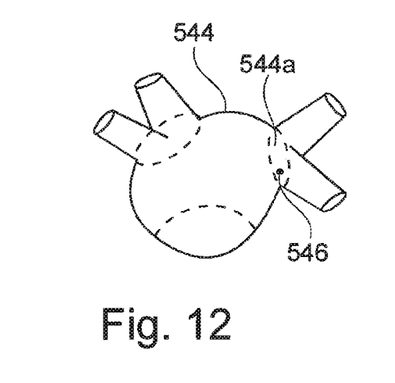

According to another example, a simplified perspective view of a left atrium is shown in FIG. 12. Thus, the left atrium represents a simplified surface representation 544 with a marker 546 and a target area 544a.

Figure 13:
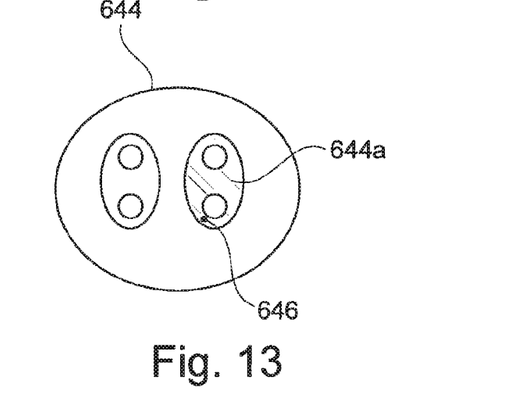

The left atrium of FIG. 12 can also be displayed in an unfolded map, shown in FIG. 13. The unfolded map represents a simplified surface representation 644 with a marker 646 and a target area 644a.

Figure 14:
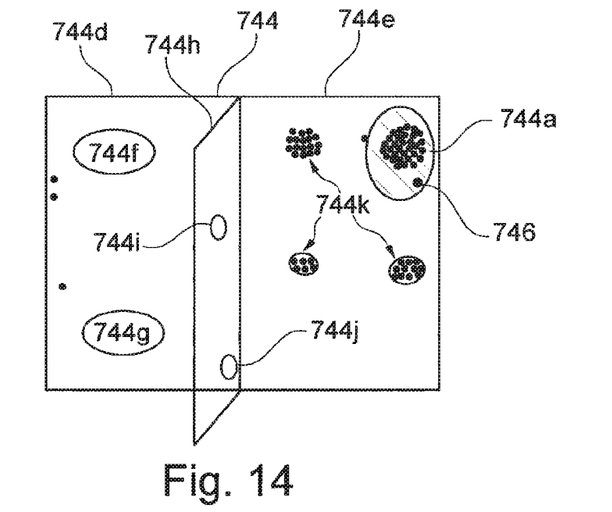

According to a further example, shown in FIG. 14, as a simplified surface representation 744, a right and left atria are shown in unfolded manner. Also here, a marker 746 as well as a target area 744a is indicated. FIG. 14 shows an unfolded map of the left 744d and right atria 744e with further anatomy information, e.g. superior vena cava 744f, interior vena cava 744g, septum 744h, fossa ovalis 744i, coronary sinus 744j and pulmonary veins 744k.

Figure 15:
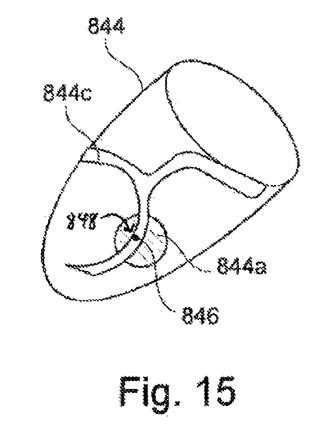

FIG. 15 shows a further example of a simplified surface representation 844 in form of a perspective wire frame of the left ventricle, for example. As can be seen, a marker 846 as well as a target area 844a is indicated. Further, the wire frame, indicated by reference numeral 844c is added by anatomy information, for example by a representation 844b of a vascular structure.

FIG. 15 also shows another aspect of the invention: According to a further exemplary embodiment of the invention, a projection axis is provided from the. detected element in the spatial geometrical data to the columned related point of location on the functional parameter surface. For example, this projection axis is used for determining a closest point. Further, the simplified surface representation in FIG. 15 is a 3D image. As can be seen, this 3D image is aligned with the projection axis. In other words, the 3D image is automatically orientated such that the visualization axis is aligned with the direction of protection of, for example the catheter/guidewire/lead to the target surface. With such an orientation, the catheter/guidewire/lead is always visible and is superimposed with its projection of the surface without any parallax error. The projection axis 848 in FIG. 15 is accordingly normal to the surface of the drawing sheet. Therefore, it becomes very easy to check that the catheter/guidewire/lead has reached its target location with respect to the surface.

Figure 16:
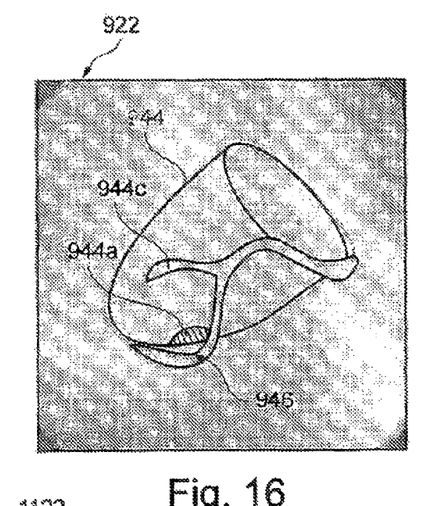

FIG. 16 shows a similar simplified surface representation 944 with a marker 946, a pattern indicating a target area 944a as well as anatomy information by a vessel representation 944c. In addition, the combination of the simplified surface representation 944 and the marker 946 is overlaid to a live image, for example a fluoroscopy image 922 which is used as the live image data 122 according to the above described embodiments.

Figure 17:
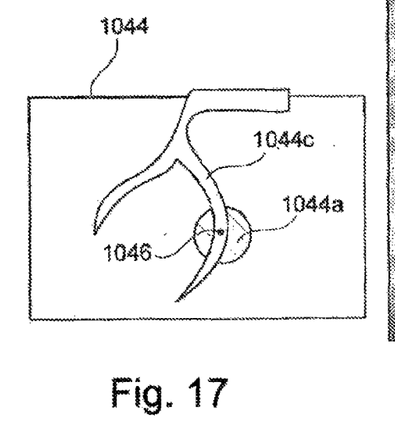

According to a further example, the simplified surface representation 844 of FIG. 15 can also be displayed in an unrolled manner, shown in FIG. 17. A simplified surface representation 1044 is combined with a marker 1046 indicating the computed predetermined related point of location. Further, it is also possible to indicate a target area with a coded pattern 1044a. According to FIG. 15, an anatomy structure, for example a vessel tree 1044c is also shown.

Figure 18:
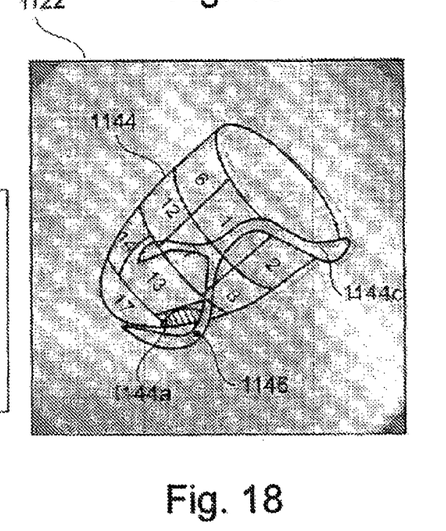

According to a further aspect, shown in FIG. 18, a fluoro image 1122 is combined with a perspective view of a left ventricle, for example according to FIG. 10. Thus, a simplified surface representation 1144 in form of the left ventricle is combined with a marker 1146. In addition, it is also possible to indicate a target area with a coded pattern 1144a. Further, as indicated with reference numeral 1144c, a vessel tree is also indicated.

Figure 19:
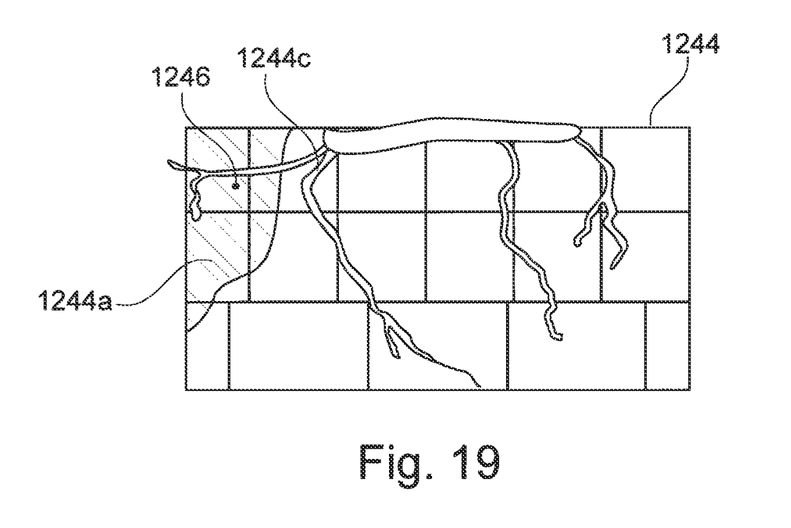

According to a further exemplary embodiment, shown in FIG. 19, an unrolled map 1244 is combined with a marker 1246 as well as a coded pattern representing a target area 1244a. Further, a vessel tree representation 1244c is overlaid to the combination.

Figure 20:
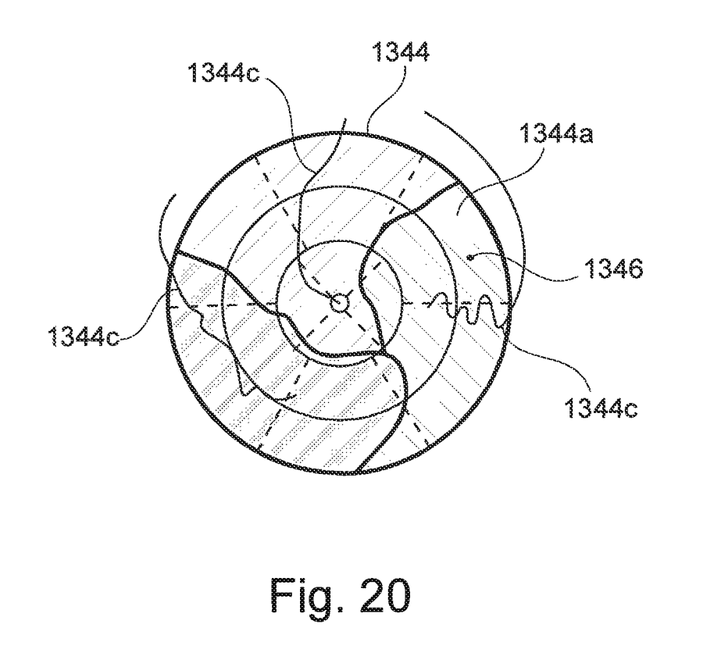

According to a further example shown in FIG. 20, a bull's-eye view 1344 is representing the simplified surface representation, which is combined with a marker 1346 as well as a target area 1344a. Further, anatomy information is overlaid in form of a vessel tree projection or modelling 1344c.

According to an aspect of the invention, for example in relation with advanced guidance methods for interventional cardiovascular procedures, a visualization of the location of catheters/guidewires/leads in relation to the target zones for ablation or pacer lead deployment is provided. It has been shown that overlay and registration of a 3D pre-operative surface onto a 2D X-ray projection requires frequent reorientation of the X-ray imaging plane to allow for a full understanding of the actual locus of interrogation, mostly because of hidden parts and/or parallax errors. The present invention therefore provides more accurate information of, e.g. the catheter position in the 3D space to the surgeon. As an advantage, the burden of navigating a catheter/guidewire/ lead in 3D towards an interrogation target is minimized.

According to one aspect, the present invention is embodied in interventional guidance software that can help identifying and reaching interrogation targets easier. Less re-orientations of the XR system are required to obtain sufficient information on 3D location of catheter/guidewire/ lead in relation to target zones.

According to one aspect, an image representing a 2D projection of a 3D area is created and displayed in real time together with a computed position of e.g. the tip of a catheter.

According to one aspect, other known projection techniques such as those usually used to get planispheres, are used alternatively. Thus, navigation takes place in such a 2D unfolded map image.

As an advantage, this approach simplifies navigation in complex 3D anatomy and helps reaching therapy targets very efficiently.

In an exemplary embodiment where 3D images are used, the method may comprise the following steps: providing a registered 3D image of the region of interest; providing a real time X-ray fluoroscopy 2D image in real time which is registered to the navigation anatomy (this image may show the invasive instrument); determining/tracking the position of the instrument in real time; there may be various ways to do this, e.g. by analyzing the fluoro image; computing a marker position of the instrument in the unfolded representation based on the position determined in the previous step; and displaying an image showing the unfolded representation including the marker at the computed position.

For example, a 2D intra-operative X-ray projection is provided of the interventional tool (e.g. catheter tip). Further, a pre or intra-operative acquisition of the 3D anatomy is provided where the interventional tool is constrained to move, e.g. coronary veins). According to another aspect, this can be replaced by another method to localize the catheter in 3D, e.g. electromagnetic localization or with two X-ray-projections at different angles. Still further, a surface representation of the intervention target is provided, e.g. left ventricule, on which can be displayed additional information, e.g. scar location and burden, mechanical function, electrical activation etc. . This surface can also be displayed in unfolded representations, e.g. a bulls-eye view.

According to one aspect, a registration of the 3D anatomy, where the catheter/guidewire/lead is moving and of the surface, where the target area is defined, is provided. The navigation anatomy and the parametric surface are registered together. If the same imaging modality is used to acquire those two elements (e.g. MRI for both LV endocardium and coronary veins), the registration is implicit. Otherwise (e.g. CTA for coronary veins and echography for LV function), a specific registration method needs to be applied (e.g. rigid transform estimated on common landmarks). Alternatively, the registration of the navigation anatomy and the parametric surface can be obtained by registering both of them independently to the 2D XR projection as mentioned above.

According to another aspect, a registration of the anatomy items as above with the live imaging used during the intervention is provided (e.g. 2D XR projection or "fluoro"). The navigation anatomy and the surface where the target area is defined are registered, separately or as a whole, to the 2D XR projection. For example, a point based 2D3D perspective registration approach can be used. After acquisition of an XR coronary venous angiogram, at least 3 marker points are determined in a 2D projection at specific anatomic locations such as vein bifurcations, CS, sharp bends in the vessel etc. The same anatomic point locations are determined in the segmented 3D coronary venous tree e.g. from cardiac MR. 2D-3D registration is performed using e.g. a 6 degree of freedom (6DOF, translation and rotation) registration approach employing an optimization. Here, the squared distances between the points in the 2D X-ray projection and the projected 3D CMR points need to be minimized(least squares of projected point distances): $\min_T \|P_{2D}^{XR} - P_{2D}^{CMR}(T)\|_2^2$ with T being the 6 DOF registration transform to be optimized, $P_{2D}^{XR}$ being the selected point set in the X-ray angiogram and $P_{2D}^{CMR}(T) = X \cdot T \cdot P_{3D}^{CMR}$ being the projected and transformed selected point set in the 3D CMR vein tree, where X represents the X-ray projection matrix. During the registration process, the perspective geometry of the XR system needs to be taken into account, which can be derived from specific calibration steps.

According to another aspect, a detection or tracking of the catheter/guidewire/lead in the live images used during the intervention is provided. This may comprise the detection or tracking of the catheter tip (or guidewire or lead tips) in real-time within the 2D XR projection. For this purpose, an appropriate template correlation filter can be used. In the specific case of CRT, a guidewire/pacer lead can be tracked within the coronary venous system.

According to another aspect, a 3D localization of the catheter/guidewire/lead is provided. This may comprises a back projection of the tracked location through the navigation anatomy where the catheter tip is constrained to navigate. Using the back projection of the tracked point in XR geometry, a corresponding 3D location (e.g. along the centreline of the coronary vein from pre-operative imaging) within the 3D navigation anatomy can be identified. For CRT, the specific location in 3D of the guidewire/lead within the coronary venous system can be determined in this way. If the back projection line does not intersect the navigation anatomy, for example due to 2D3D mis-registration or motion, the closest (or the statistically most likely) point in the constraining anatomy can be used. Deformations due to breathing and cardiac motion can be taken into account with template-based breathing motion tracking, ECG gating or other motion compensation approaches.

According to a further aspect, another method is used for the 3D location of the catheter tip, e.g. electromagnetic localization (EM localization) or with 2 XR projections at different angles. In this case, there is no need for the constraining navigation anatomy and this invention can be applied to navigation in larger anatomical regions such as cardiac chambers (left atrium for AF ablation or left ventricule for VT ablation).

According to another aspect, a projection of the catheter/guidewire/lead onto the surface where the target area is defined is provided. This may comprise the calculation of the closest point of the determined 3D location to a target location on the 3D parametric surface. In the specific case of CRT, the closest point on the left-ventricular (LV) surface (assuming it is represented by a discrete mesh), from the current 3D location within the coronary venous system is determined by: $\min_i \|P_{3D}^{lead} - P_{3D}^{LV-mesh}(i)\|_2^2$ where $P_{3D}^{lead}$ is the 3D point within the venous system and $P_{3D}^{LV-mesh}(i)$ is the 3D coordinate of the LV mesh at vertex i.

According to another aspect, a displaying of the catheter/guidewire/lead and the target area on the simplified view (unfolded 2D view or automatically oriented 3D) is provided. Preferably, the navigation anatomy, e.g. the coronary veins, are also displayed on the same view.

Once the 3D location of the catheter tip $P_{3D}^{lead}$ and its closest target point on the parametric surface $P_{3D}^{mesh}$ are both available, we propose new ways to display automatically the navigation information in the easiest way. The first proposal is to orientate the 3D view automatically so that $(P_{3D}^{lead}, P_{3D}^{mesh})$ is aligned to the visualization axis. The second proposal is to display $P_{3D}^{mesh}$ on the unfolded map, so that one can directly see its position with respect to the information displayed in the map. Additionally, if available, the navigation anatomy can also be overlaid on top of the unfolded map, providing information on the possible paths for the catheter tip.

For the specific case of CRT, the closest point on the LV with regard to the tracked guidewire/lead location within the coronary venous system is displayed in a bulls-eye plot as already mentioned. According to the American Heart Association, the LV can be separated into 17 segments, 6 basal, 6 equatorial and 5 apical segments. Functional Ultrasound or MR allows the visualization of important functional information in such bulls-eye plots. This way, the current location of the guidewire/lead can be visualized in real-time in relation to target spots in the bulls-eye. For CRT, the bulls-eye should practically contain information such as mechanical activation, scar burden and electrical activation.

According to another aspect, the invention can be used for CRT or any other interventional procedure requiring catheter/lead/guidewire position in relation to anatomy and specific parameters i.e. function, scar burden, electrical activity etc. (e.g. ventricular tachycardia VT ablation, stem cell injection etc.). If applied for VT ablation, the bulls-eye can contain information such as scar burden and electrical activation. If applied for atrial fibrillation ablation, a 2D surface map of the left atrium can be used instead of a LV bulls-eye, indicating the ostia of the pulmonary veins.

In another exemplary embodiment of the present invention (not shown), a computer program or a computer program element is provided i.e. characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus.

The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention (not shown), a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage.

The invention claimed is:

1. A method for visualizing information of an object of interest, the method comprising the steps of:
   a) providing pre-navigation data of a region of interest of an object wherein the pre-navigation data comprises spatial geometrical data and a functional parameter surface in correspondence to the spatial geometrical data;
   b) acquiring live image data of the region of interest;
   c) utilizing the live image data to detect an instrument in the live image data;
   d) determining spatial relation of the pre-navigation data and the live image data;
   e) determining the position of the detected instrument in the spatial geometrical data, which determining is based on the spatial relation, and computing a predetermined related point of location on the functional parameter surface;
   f) generating a combination of a simplified surface representation of the region of interest, which simplified surface representation is based on a visualization of the functional parameter surface, and a marker indicating the computed predetermined related point of location; wherein the simplified surface representation is an unfolded map image; and
   g) displaying the combination as navigation guidance.

2. The method according to claim 1, wherein said determining based on said spatial relation in step e) determines a point in said spatial geometric data, said predetermined related point of location being a closest point on the functional parameter surface to the determined point.

3. The method according to claim 1, wherein the detection of the instrument comprises determining the 2D position of the instrument in the live image data and for determining the position in step e), the detected 2D position is mapped to the spatial geometrical data by a direct projection line.

4. The method according to claim 1, wherein step e) comprises a back projection) of the determined position through the spatial geometrical data, to estimate spatial position of the instrument.

5. The method according to claim 4, wherein in case that the back projection does not intersect with the anatomy according to the spatial geometrical data, the closest or statistically most likely point in the anatomy is used.

6. The method according to claim 1, wherein a projection axis from the detected instrument in the spatial geometrical data to the computed related point of location on the functional parameter surface is provided; further including the step of displaying a 3D image of said region of interest, said 3D image being aligned with the projection axis.

7. The method according to claim 1. wherein step f) comprises combining navigation anatomy with the simplified surface representation.

8. The method according to claim 1, wherein the navigation anatomy comprises a projection of the vascular structure.

9. The method according to claim 1, wherein the navigation guidance is a 2D representation comprising functional parameter surface information and 3D positioning information of the instrument in relation to the region of interest.

10. The method of claim 1, wherein said instrument is an invasive instrument.

11. A device, for visualizing information of an object of interest, comprising:
a processor;
an interface unit; and
a display;
wherein the interface unit comprises a circuit configured for providing pre-navigation data of a region of interest of an object, wherein the pre-navigation data comprises spatial geometrical data and a functional parameter surface in correspondence to the spatial geometrical data; and for providing live image data of the region of interest;
wherein said processor comprises a circuit configured for utilizing the live image data to detect an instrument in the live image data; for determining spatial relation of the pre-navigation data and the live image data; for determining the position of the detected instrument in the spatial geometrical data, which determining is based on the spatial relation, and for computing a predetermined related point of location on the functional parameter surface; and for generating a combination of a simplified surface representation of the region of interest, which simplified surface representation is based on a visualization of the functional parameter surface, and a marker indicating the computed predetermined related point of location; wherein the simplified surface representation is an unfolded map image; and wherein the display is adapted to display the combination as navigation guidance.

12. A medical imaging system for visualizing information of an object of interest, comprising: is device according to claim 11; and image acquisition apparatus; wherein said device is configured for, via the image acquisition apparatus, acquire the live image data of the region of interest.

13. The device of claim 11, further comprising a processor unit that includes said processor.

14. The device of claim 13, wherein said interface unit serves as a user interface unit, and said processor comprises a medical imaging processor.

15. The device of claim 14, wherein said medical imaging processor comprises an X-ray imaging processor.

16. The device of claim 11, said circuit being realized in a solid state medium.

17. The device of claim 11, wherein said instrument is an invasive instrument.

18. A non-transitory computer readable medium embodying a program for visualizing information of an object of interest, said program having instructions executable by a processor for performing a plurality of acts, from among said plurality there being the acts of:
a) providing pre-navigation data of a region of interest of an object wherein the pre-navigation data comprises spatial geometrical data and a functional parameter surface in correspondence to the spatial geometrical data;
b) acquiring live image data of the region of interest;
c) utilizing the live image data to detect an instrument in the live image data;
d) determining spatial relation or the pre-navigation data and the live image data;
e) determining the position of the detected instrument in the spatial geometrical data, which determining is based on the spatial relation, and computing a predetermined related point of location on the functional parameter surface;
f) generating a combination of a simplified surface representation of the region of interest, which simplified surface representation is based on a visualization of the functional parameter surface, and a marker indicating the computed predetermined related point of location; wherein the simplified surface representation is an unfolded map image; and
g) displaying the combination as navigation guidance.

19. The computer readable medium of claim 18, wherein said instrument is an invasive instrument.

* * * * *